(12) United States Patent
Pacetti

(10) Patent No.: US 6,419,657 B1
(45) Date of Patent: Jul. 16, 2002

(54) FLOW REGULATOR VALVE TO OPTIMIZE STENT DEPLOYMENT AND METHOD OF USING THE SAME

(75) Inventor: Stephen Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 154 days.

(21) Appl. No.: 09/644,392

(22) Filed: Aug. 22, 2000

(51) Int. Cl.[7] .................. A61M 75/00; A61M 25/00

(52) U.S. Cl. ............... 604/99.04; 604/247; 604/920; 137/513.3

(58) Field of Search .................. 604/99.01, 99.02, 604/99.03, 99.04, 246, 247, 920; 137/512, 513.3, 513.5, 513.7

(56) References Cited

U.S. PATENT DOCUMENTS

| | | | |
|---|---|---|---|
| 4,429,856 A | 2/1984 | Jackson | 604/247 |
| 4,857,054 A | 8/1989 | Helfer | 604/99.03 |
| 4,932,938 A | 6/1990 | Goldberg et al. | 604/99.04 |
| 5,201,707 A | 4/1993 | Kanai | 604/99.02 |
| 5,254,092 A | 10/1993 | Polyak | 604/247 |

*Primary Examiner*—Harry B. Tanner
(74) *Attorney, Agent, or Firm*—Fulwider Patton Lee & Utecht, LLP

(57) ABSTRACT

An apparatus for regulating flow of an inflation fluid to a stent delivery balloon. A valve, which is situated in the flow path of the inflation lumen, regulates the flow of liquid used to inflate and deflate the balloon. The valve performs to restrict flow and to respond to pressure applied to assure a desired inflation rate when fluid is flowing toward the delivery balloon. On deflation, when fluid is flowing away from the delivery balloon, the valve is designed to offer little or no resistance, allowing the balloon to be deflated quickly.

21 Claims, 4 Drawing Sheets

FLOW REGULATOR VALVE TO OPTIMIZE STENT DEPLOYMENT AND METHOD OF USING THE SAME

BACKGROUND OF THE INVENTION

The present invention generally relates to intravascular balloon catheters, and more particularly, to a flow regulator valve for regulating the flow of inflation fluid being delivered to a stent delivery balloon catheter.

Angioplasty is a procedure where a balloon is positioned in an artery at the site of a lesion and expanded in order to compress the lesion and enlarge the restricted area in the artery. In this procedure, a balloon is formed on one end of a catheter. The catheter is inserted transluminally to maneuver the balloon through the patient's vasculature to the site of the lesion. When the uninflated balloon is properly positioned at the lesion, the balloon is inflated to dilate the restricted area.

In these procedures there may be restenosis, also referred to as recurrent stenosis, of the artery. Restenosis may require another angioplasty procedure, a surgical bypass operation, or some method of repairing or strengthening the area. To reduce the risk of restenosis and strengthen the area, a physician can implant an intravascular prosthesis for maintaining vascular patency, typically called a stent.

A stent is a device used to hold tissue in place or to provide support for a graft or tissue joined while healing is taking place. Stents are typically implanted by use of a catheter which is inserted at an easily accessible location and then advanced through the vasculature to the deployment site. The stent is initially maintained in a radially compressed or collapsed state to enable it to be maneuvered through a body lumen. Once in position, the stent is usually deployed either automatically by the removal of a restraint, or actively by the inflation of a balloon about which the stent is carried on the deployment catheter.

In reference to balloon catheter stents, a variety of devices are known in the art for use as stents, including coiled wires and wire mesh sleeves in a variety of patterns that are configured to be crimped onto a balloon catheter. Typically, the stent is mounted on and crimped to the balloon portion of the catheter. The catheter is introduced transluminally with the stent mounted on the balloon. The balloon is then inflated to expand the stent to a larger diameter to implant it in the artery at the lesion. An optimal clinical outcome requires correct sizing and deployment of the stent. An under deployed stent will have struts that are not in good apposition with the arterial wall.

Struts of the stent which are not properly deployed can create disturbed blood flow, stagnant regions of flow, and consequently create a high risk of thrombosis. Not being pressed into the arterial wall, they are unlikely to be endothelialized. This creates a long-term risk of thrombosis. Overexpanded stents produce over sizing or over expansion and consequent damage to the arterial wall.

The damage can span a range from simple penetration of the intima to tearing of the IEL (inner elastic lamina), media EEL (outer elastic lamina), and adventitia. Damage of the vessel wall has been shown to stimulate an inflammatory response that is linked to greater neointimal proliferation. Consequently, excessive vessel damage is believed to be a factor for the presence and degree of instent restenosis.

A common theme in PTCA (Percutaneous Transluminal Coronary Angioplasty), with or without stenting, is that a bigger lumen is better. However, this concept is tempered by the fact that vessel damage must be avoided. Certainly, the two biggest complications of stents, namely, restenosis and SAT (subacute thrombosis), are directly affected by the accuracy of stent deployment.

Another important aspect of stent deployment is the rapidity with which the stent is expanded. For balloon deployed stents, this is controlled by balloon inflation. Inflation is usually achieved through manual inflation-deflation devices (indeflators) or a "smart" indeflator unit that possesses some automation. In general, slower inflation is better. During inflation, kinetic effects create non-equilibrium conditions. For example, the friction of the balloon against the stent is affected by inflation rate. The stents, being made of metal also, have elastic versus plastic deformation behavior. A fast inflation/deflation cycle can result in higher levels of stent recoil. Inflation speed affects the uniformity of stent deployment along its length. Often, the distal and proximal ends of the balloon inflate first. A dumbell or dog bone shape is created which exerts a net inward force on the stent. Consequently, fast stent inflation may lead to more stent shortening. Ideally, the stent is deployed uniformly, with an even spreading of the struts around the periphery. Fast deployment is believed to increase the likelihood of struts being clustered together in sections and overexpanded in others.

In addition to the deployment problems listed above, areas where the stent is overexpanded have an increased chance of plaque prolapse. There are many potential reasons why inflation speed affects stent expansion. Catheter balloons can be folded in a non-uniform way. Balloon folds can get stuck or "caught" on stent struts. The lesion environment is rarely uniform, or with a perfectly concentric plaque. Lesions are typically eccentric, sometimes with fibrous or calcified focal regions. Consequently, the resistance to radial expansion of the balloon may be greater in certain directions resulting in an eccentric deployment. Lastly, in clinical practice, the process of stent implantation can become routine. Such familiarity often leads to shorter procedural times which tend to beneficial for the patient except for steps, such as stent inflation, where faster is not always better.

An improved intravascular stent delivery device is therefore needed to overcome the problems in the prior art. More particularly, the improved stent delivery device must provide a higher degree of safety than conventional delivery devices and must be comparatively inexpensive to manufacture. The present invention satisfies these and other needs.

SUMMARY OF THE INVENTION

Briefly, and in general terms, the present invention provides a new and improved apparatus and method to be used with balloon catheters. More specifically, the apparatus and accompanying method provide a flow regulator for regulating flow of an inflation fluid to a stent delivery balloon catheter.

In general terms, this invention is characterized by a valve regulator in fluid communication with the expandable portion, usually a balloon, of an inflatable balloon catheter. Situated in the flow path of the inflation lumen, the valve regulates the flow of liquid used to inflate the balloon. The valve is constructed to restrict flow and to respond to pressure applied to assure a desired inflation rate. On deflation, the valve offers little or no resistance, allowing the balloon to be deflated quickly. The present invention can be particularly useful when used with a stent delivery catheter to achieve uniform expansion of the stent at a desire inflation rate.

In one aspect of the present invention, the regulator incorporates a body having on its distal end a connector for connection to the balloon and on its proximal end a connector defining a control chamber for connection with an inflator. The chamber is configured at the distal end of the device with an orifice. A restrictor in the chamber is operable in response to the fluid flowed distally toward an orifice to cooperate with the orifice to form a predetermined flow area for flow therethrough at a certain flow rate. When fluid is flowed in the proximal direction through the chamber, the restrictor moves away from the orifice to forming a second flow area larger than the first flow area for flow in the opposite direction and at a greater flow rate.

The restrictor can include a poppet carried floatably in the chamber and shiftable from one end to the other to engage respective proximal and distal stops. The poppet may be round and perforated to provide for flow therethrough at a controlled rate. The poppet may be compressible so that, upon application of high pressure, it will expand laterally to reduce the flow area therearound to reduce the flow rate. Travel of the poppet in the opposite direction may be limited by contact with the axial ends of radial fins arranged in a radial array.

The present invention also contemplates a method of implanting an expandable intra-luminal stent. First, the stent is delivered by an inflatable delivery balloon incorporating a flow control valve. The valve is of the type limiting flow of a selected inflation fluid in one direction toward such balloon. In this fluid flow direction, the flow rate is controlled so as to expand the stent at a selected rate. When the fluid is flowed in the opposite direction, the rate is much greater so as to quickly deflate the balloon. Additionally, it is possible to control the fluid flow in one direction by reducing the flow rate in response to increased fluid pressure.

This invention may be employed to control the expansion, via an inflation balloon, of any endoluminal stent. The stent can be intended for the coronary, iliac, carotid, neurological, renal, or other peripheral vasculature. There are no restrictions on the type of stent, size, or its placement. The present invention can be a separate device which can be attached to an inflation device and the balloon catheter, or it can be built directly into, for example, the proximal hub of the catheter. The present invention also can be build directly into the inflation device, if desired.

These and other features and advantages of the present invention will become apparent from the following detailed description, taken in conjunction with the accompanying drawings, which illustrate, by way of example, the features of the invention.

DETAILED DESCRIPTION OF THE PREFERRED EMBODIMENTS

Briefly, and in general terms, the present invention provides a new and improved apparatus and method to be used with balloon catheters. More specifically, the apparatus and accompanying method provide a flow regulator for regulating flow of an inflation fluid in a stent delivery balloon catheter.

In less general terms, this invention incorporates a regulator valve in the proximal adapter of a balloon inflation catheter. Situated in the flow path of the inflation lumen, the valve regulates the flow of liquid used to inflate the balloon. The valve is adapted to restrict flow and to respond to increases in pressure which may be applied by an inflation device to assure a desired inflation rate. On deflation, the valve is designed to offer little or no resistance to fluid evacuation, allowing the balloon to be deflated quickly.

Figure 1:
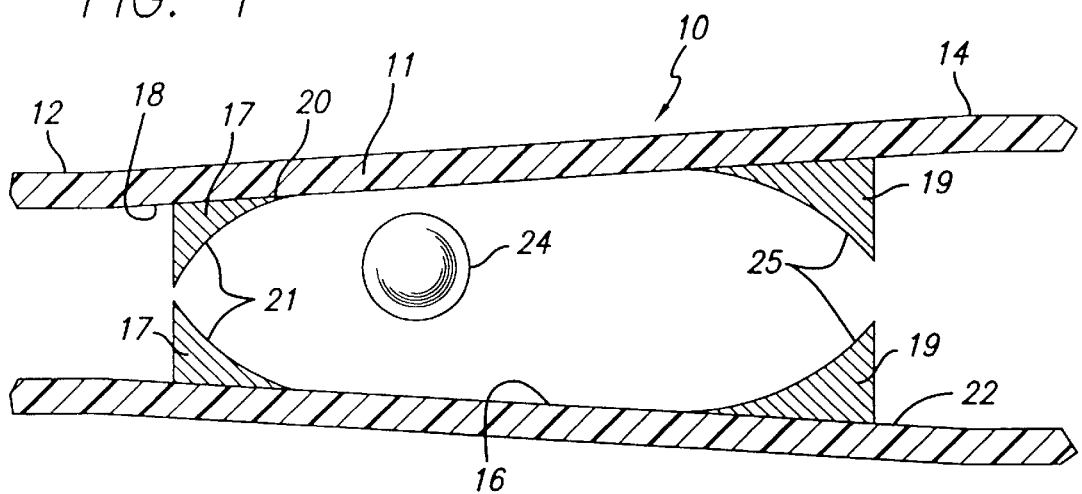
FIG. 1 is a longitudinal sectional view of a regulator valve made in accordance with the present invention.

Referring now to the drawings, in which reference numerals represent like or corresponding elements across the drawings, and particularly to FIG. 1, there is shown a flow regulator valve 10 which includes a substantially conical, tubular housing 11 with a distal connector 12 and proximal connector 14. Due to the conical shape of the housing, the proximal connector 14 has a larger diameter than the distal connector 12.

In the particular embodiment described herein, the housing 11 includes a conical control chamber 16 tapering downwardly to the left towards the distal extremity and configured with a distal orifice 18 of a predetermined diameter. The housing 11 is formed on its distal and proximal extremities with an annular array of longitudinally projecting, radial proximal and distal fins 17 and 19 generally arranged in an annular pattern. Such fins 17 and 19 are somewhat triangular shape in longitudinal sectional view but are formed with respective curved stop edges 21 and 25 which curve to angle towards the center of the chamber and radially inwardly toward the longitudinal center line of the chambers so as to form respective proximally facing stops which limit the longitudinal extent of the chamber itself as will be discussed hereinafter.

A spherical poppet, generally designated 24, is floatably positioned in the control chamber 16 to be carried longitudinally therein with the flow of inflation fluid. If desirable, the poppet may be floatable in the inflation fluid, it being of a sufficient weight and size so as to be driven longitudinally within the control chamber 16 as the inflation fluid is being pressurized or de-pressurized.

In operation, it will be appreciated that the flow regulator valve 10 of the present invention may be connected in line with a deployment balloon to be utilized in carrying a stent into position and deployment thereof. In some configurations, the regulator valve could be incorporated directly in the proximal hub of the balloon catheter. In still others, the regulator valve could be constructed as a separate component which is attachable to a balloon delivery catheter or inflation pump. It should also be appreciated that the invention can be incorporated into an inflation device as well.

Figure 2:
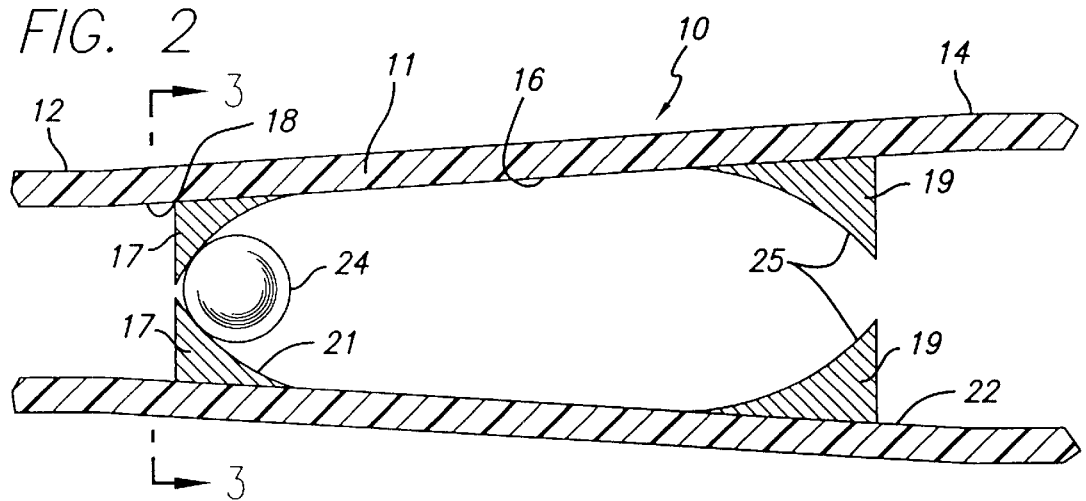
FIG. 2 is a longitudinal sectional view, similar to FIG. 1, with the poppet positioned at the distal end of the regulator housing.
Figure 3:
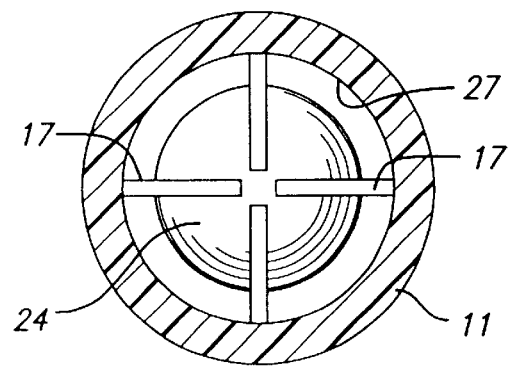
FIG. 3 is a cross-sectional view of the distal end of the flow valve shown in FIG. 2 taken along line 3—3.

It will be appreciated that during inflation of the balloon, the inflation fluid will flow from right to left, as viewed in FIG. 1, from the proximal connector 14 to the distal connector 12. As the fluid flows through the control chamber 16, it will carry the ball poppet 24 therewith to drive the ball poppet to the left to the position shown in FIG. 2. The ball poppet 24 will engage the arcuate and sloping stop edges 21 of the respective distal fins 17 to be slid longitudinally thereacross and driven to the longitudinal center of the chamber 16 to position the major diameter thereof in fixed relation relative to the distal orifice 20. With the ball poppet 24 so positioned, the annulus 27 (see FIG. 3) formed between the interior wall of the control chamber 16 and major diameter of the ball poppet 24 will define a restricted flow area. Thus, depending on the source pressure of the pressurization fluid, the flow rate through this annulus 27 will be dictated by the pressure drop across the ball poppet 24 thereby dictating the rate of balloon pressurization. This serves to assure that the balloon is inflated at a controlled inflation rate to control the deployment of the stent accordingly.

Figure 4:
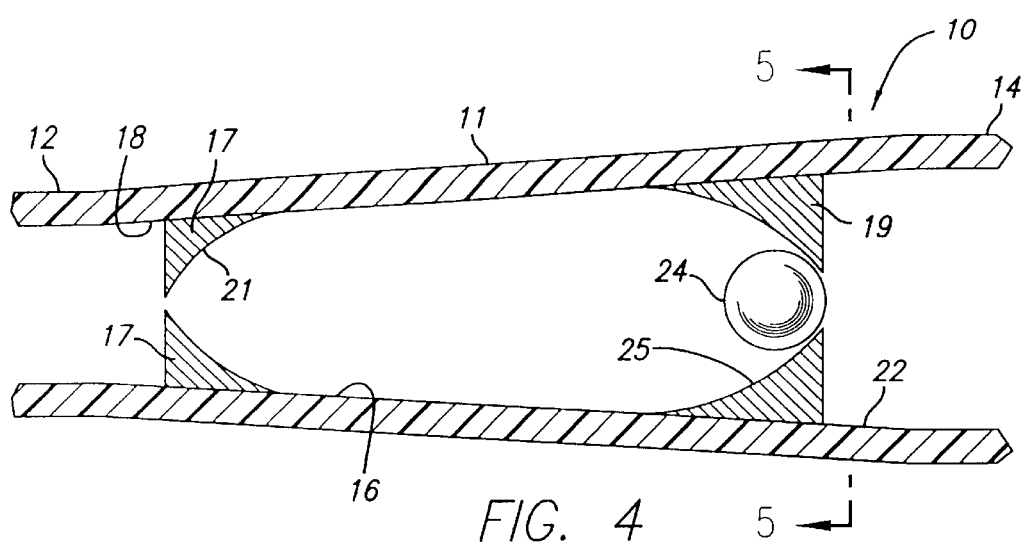
FIG. 4 is a longitudinal section view, similar to FIG. 1, with the poppet positioned at the proximal end of the regulator housing.
Figure 5:
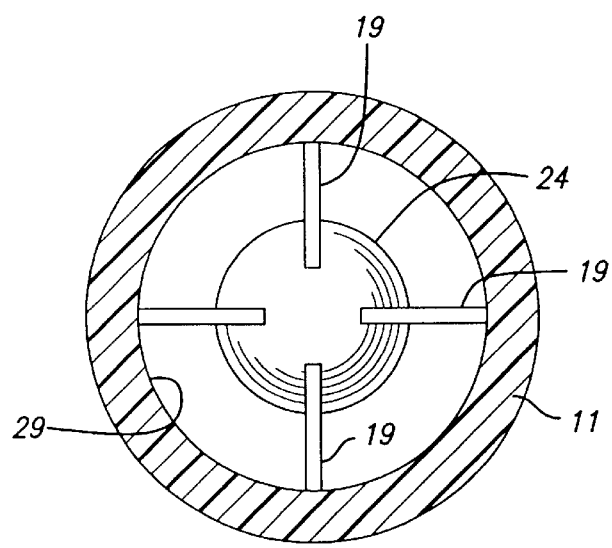
FIG. 5 is a cross-sectional view of the proximal end of the flow regulator valve shown in FIG. 4 taken along line 5—5.
Figure 11:
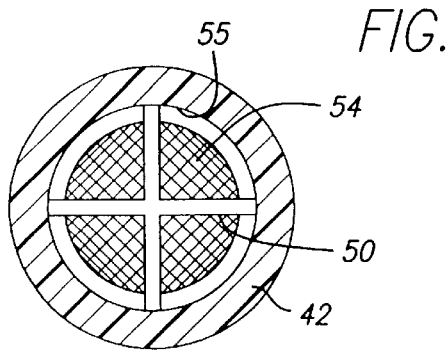
FIG. 11 is a cross-sectional view of the distal end of the flow valve shown in FIG. 10 taken along line 11—11.

Once the stent has been deployed, the valving controlling pressurization may be stopped and a vent valve opened to purge inflation fluid from the balloon. After the vent valve is opened, active negative pressure is applied to the connection 14 to help deflate the balloon. In this manner, the pressure source, commonly called an indeflator, is initially utilized to pull a partial vacuum on the proximal connection to actively start the venting process. This application of a partial vacuum serves to reduce the pressure in the proximal connector fitting 14, thus allowing the pressure in the deployment balloon to flow back through the distal annulus 27 about the poppet 24 to carry the poppet longitudinally to the right, as shown in FIG. 1. As the poppet 24 travels proximally in the conical chamber 16, the annular space 27 increases dramatically to provide for increased flow rate, causing the balloon to rapidly deflate. As the ball poppet 24 reaches the proximal extent of the control chamber 16, it will engage the stop edges 25 of the proximal fins 19 causing the ball poppet 24 to again be centered along the longitudinal center line of the chamber 16 at the position shown in FIG. 4. This serves to center the ball poppet 24 with its major diameter in diametrical alignment with the relatively large proximal to orifice 22 so that any continued flow through the annulus 29 (see FIG. 5) formed between the wall of the body 11 and major diameter of the ball poppet 24 will accommodate a high rate of fluid flow, thereby providing for continued rapid balloon deflation so that the balloon can be quickly deflated and removed transluminally from the patient's vasculature.

Figure 6:
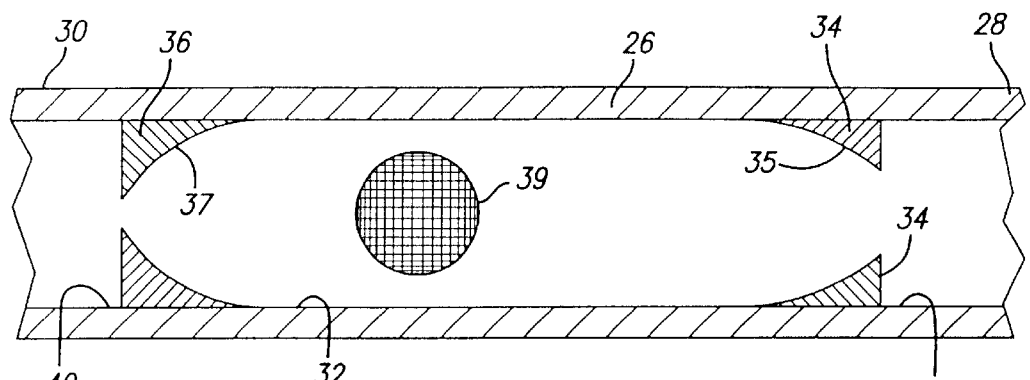
FIG. 6 is a longitudinal sectional view of a second embodiment of a flow regulator valve of the present invention.
Figure 7:
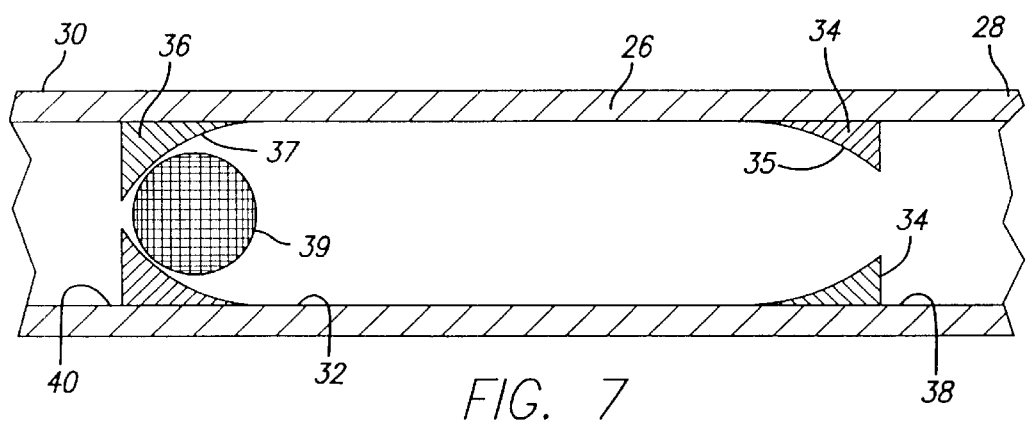
FIG. 7 is a longitudinal sectional view, similar to FIG. 6, with the poppet positioned at the distal end of the regulator housing.
Figure 8:
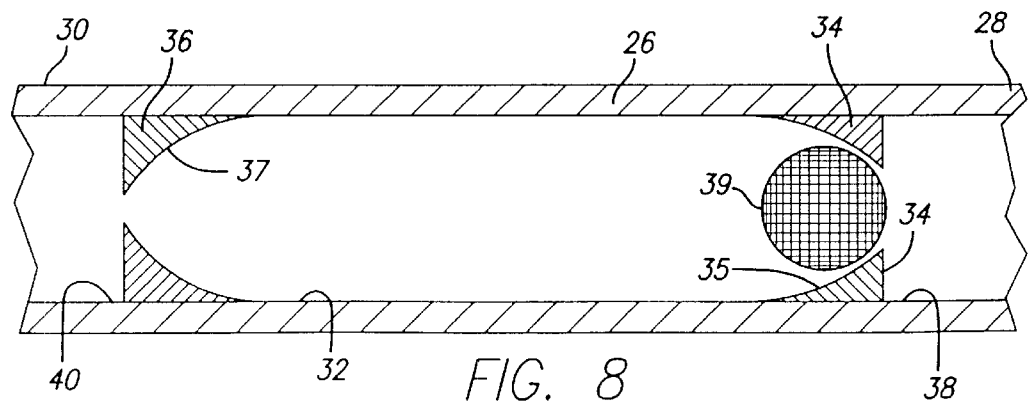
FIG. 8 is a longitudinal sectional view, similar to FIG. 6, with the poppet positioned at the proximal end of the regulator housing.

Referring now to FIGS. 6 through 8, a second embodiment of the flow regulator of the present invention includes, generally, a housing 26 formed with a longitudinal cylindrical control chamber 32. While the housing 26 is disclosed herein as cylindrical, it will be appreciated that it too could be conically shaped or of any other desired configuration. The body is formed at the proximal end with a proximal fitting 28 for connection to a pressurization tube and is further configured with a radially inwardly projecting shaped flange 34 configured with a radially inwardly and longitudinally tapering stop wall 35 terminating at its proximal end in a circular large diameter orifice 38. This housing 26 is formed at the distal extremity with an interior annular flange 36 also having a distally converging annular inner stop surface 37 terminating in a small diameter distal orifice 40.

Housed within the control chamber 32 is a floatable porous spherical poppet 39 configured with diametrical through passages interspersed thereabout for flow of pressurization fluid diametrically in any direction therethrough.

In operation, it will be appreciated that the flow regulator of FIGS. 6–8 may be connected in the pressurization system as described above with the connector 30 incorporated in the balloon or otherwise in fluid communication with the balloon. Once the site is reached, the balloon may be pressurized by applying a pressure to the proximal end of the regulator valve (via a pressure source instrument) thus allowing fluid to flow from right to left as viewed in FIG. 6. This flow will carry the ball poppet 39 to the left, as viewed in FIG. 6, to the position shown in FIG. 7, engaging the stop flange surfaces 37 to be driven to the longitudinal center of the body 26. Then, fluid flow through the orifice 40 will be dictated by the composite diametrical flow paths through the porous poppet 39 as dictated by the pressure drop across this poppet 39. This will provide for controlled flow into the balloon and controlled inflation thereof consumately providing for controlled deployment of the stent.

Once the stent has been fully deployed, pressurization may be discontinued to allow for the evacuation of the inflation fluid from the balloon via the proximal end of the chamber 26. This will then cause the inflation fluid to flow in the reverse direction to the chamber 32 from left to right, as viewed in FIG. 7. The fluid flow will then carry the porous poppet 39 to the position shown in FIG. 8 to be centered in the large diameter orifice 38. It will be appreciated that, in the meantime, as the flow is initially vented from the proximal end of the flow regulator, the annular space about the porous poppet will provide an additional flow area to increase the rate of balloon deflation. In the event deflation is not totally completed by the time the porous poppet 39 shifts totally to the right as shown in FIG. 8, the relatively large diameter orifice 38 will facilitate further high rate of deflation to rapidly deflate the balloon and clear it for removal. As will be appreciated by those skilled in the art, this feature can be important in the case of an emergency or other steps in the technique where rapid deflation becomes extremely important.

Referring now to FIGS. 9–13, the flow regulator shown therein is in the form of a housing 42 defining a longitudinal control chamber 48 which houses a resilient spherical poppet 54. The regulator valve includes distal and proximal connectors 44 and 46. An array of diametrical retainer fins 50 located at the distal end of the housing 42 form flow interstices 58 having a cross-sectional area smaller than the diameter of the ball poppet 54 to prevent the poppet from escaping. Diametrical fins 52 formed at the proximal end of the housing 42 cooperate to hold the poppet 54 captive in the control chamber 48.

Figure 9:
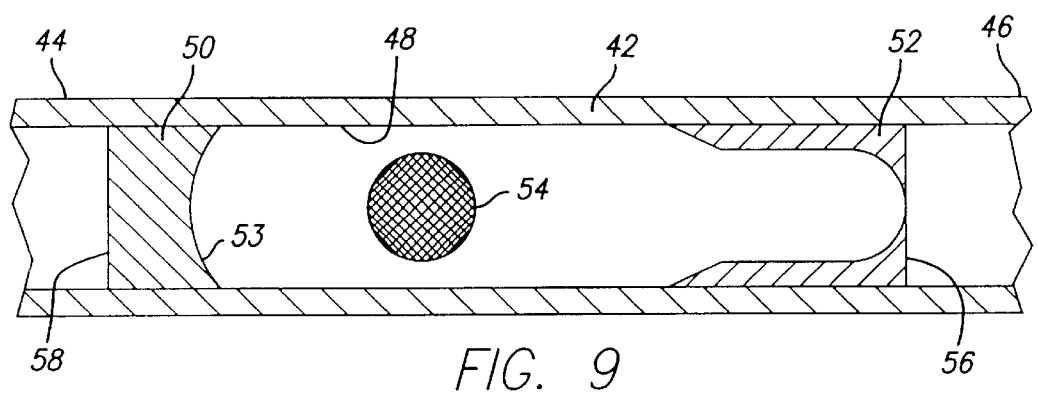
FIG. 9 is a longitudinal sectional view of a third embodiment of a flow regulator valve of the present invention.
Figure 10:
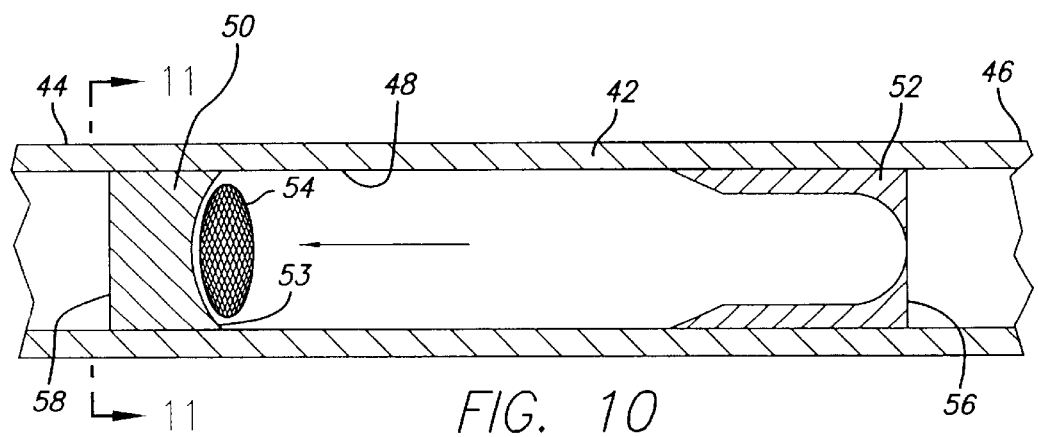
FIG. 10 is a longitudinal sectional view, similar to FIG. 9, with the poppet positioned at the distal end of the regulator housing.
Figure 12:
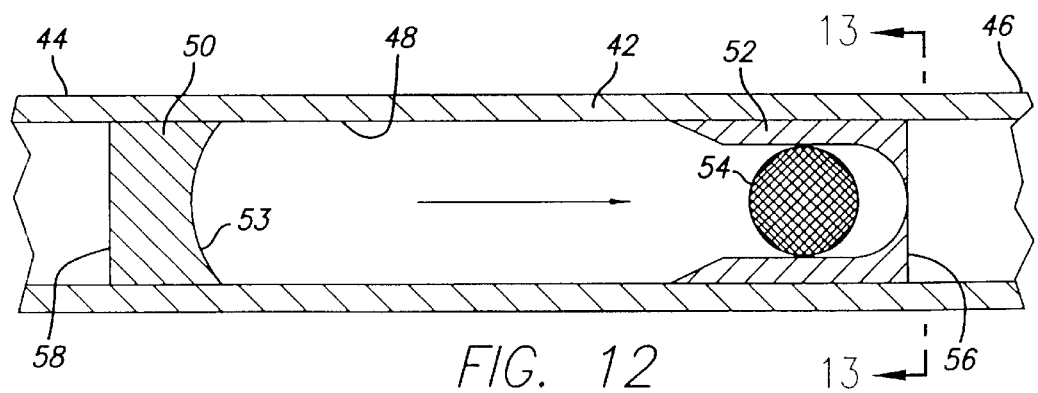
FIG. 12 is a longitudinal sectional view, similar to FIG. 9, with the poppet positioned at the proximal end of the regulator housing.

The ball poppet 54 is constructed to normally assume a spherical shape (FIG. 9) but is deformable under pressure to the somewhat flattened shape shown in FIG. 10 to assume an enlarged transverse diameter.

It will be appreciated that the operation of the flow regulator shown in FIG. 9 is similar to that described hereinabove except that during inflation the poppet is driven to the left, as viewed in FIG. 10, to engage the transversely projecting stop surface 53 of the fins 50 to stop travel thereof. Then, as the pressurization pressure of the fluid builds up, fluid flow continues to the annular space 55 (see FIG. 11) between the major diameter of such poppet 54 and the interior wall of the chamber 48, the pressure drop across such poppet will be increased thereby causing the poppet 54 to flatten out in the diametrical direction, as shown in FIG. 10. This then serves to decrease the annular space 55 between the major diameter of the poppet 54 and interior wall of the chamber 48, (see FIGS. 10 & 11), thus decreasing the flow rate of the pressurizing fluid to thereby control the rate of inflation for the balloon.

Figure 13:
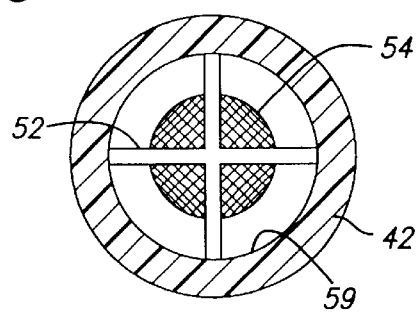
FIG. 13 is a cross-sectional view of the proximal end of the flow valve shown in FIG. 12 taken along line 13—13.

Fluid flow through the regulator valve will continue to inflate the balloon at a controlled rate until such time as the stent is deployed to the desired configuration. Thereafter, the pressurization source may be adjusted to discontinue pressurization and initiate venting. Evacuation of the fluid at the proximal end 46 will result in equalization of pressure across the poppet 54 to cause it to return to its normal spherical condition, thus increasing the annular flow area thereabout thus providing increased fluid flow rate from the balloon to achieve rapid deflation of the balloon. As can be seen from FIGS. 11 and 13, the ball poppet 54 resumes its spherical shape and engages the diametrical fins 52 formed at the proximal end of the housing 42. As can be seen in FIG. 13, there is sufficient annular space 59 for the fluid to flow past the ball poppet 54 to allow for a quick evaluation of the inflation fluid from the balloon portion of the catheter.

While a particular form of the invention has been illustrated and described, it will also be apparent to those skilled in the art that various modifications can be made without departing from the spirit and the scope of the present invention. More particularly, the present invention can be embodied in a conventional check valve with a slight modification. The modification would be to form a small flow area for fluid to flow when the valve is in the closed position. This modification would enable the device to have the properties of a leaky check valve.

A flapper-type valve can be incorporated into the design without departing from the scope of the invention. In this configuration, the regulator valve would be substantially tubular. Inside the regulator, a control chamber would be formed with both proximal and distal ends. A substantially flat and circular valve would be positioned within the chamber so as to be capable of blocking flow. The valve would be positioned such that it tilts open to allow fluid to flow in one direction. When fluid flows in the other direction, the valve would shut and only allow fluid to flow through a weep hole incorporated into its surface. In this configuration, the valve would perform essentially the same function as the three embodiments described above.

All other types of valves or devices which permit fluid to flow relatively unrestricted in one direction while greatly restricted in the opposite direction are also included within the scope of this invention when they are used for the purpose of inflating and deflating a balloon catheter used in a stent delivery system.

The flow regulator can also be positioned away from the delivery balloon of the delivery balloon catheter and formed separate from such catheter. In this form, the proximal end of the regulator would couple to the inflation device while the distal end of the regulator valve would be coupled to the delivery balloon catheter.

The manner of construction and the materials used for the device are also variable without departing from the scope of the invention. For instance, the regulator housing may be formed from plastics such as polyvinylchloride, polycarbonate, polysulfone, polystyrene, ABS, polyacetal, or polymethylmethacrylate. Metals such as aluminum alloy, stainless steel or titanium are suitable. Internal components such as poppet balls may be made from the same materials listed above with additional plastics such as polyethylene, polypropylene, polytetrafluoroethylene, or polyvinylidene flouride, being suitable. Elastomeric poppets, diaphrams, or flaps can be made from a wide variety of elastomeric materials including, but limited to, silicone, viton, neoprene, SBR rubber, butyl rubber, and polyurethanes. Methods of fabrication are familiar to those skilled in the art for metal, plastic and elastomeric fabrication. Other suitable methods of manufacture would include injection molding, extrusion, casting, and machining.

It should be appreciated that the present invention can be used in accordance with stent delivery catheters in order to achieve uniform deployment of the stents. The present invention also can be utilized with balloon catheters which are utilized in angioplasty in order to provide a uniform balloon expansion to compress a stenosis within the patient's body lumen. Thus, the present invention is quite versatile in that it can be utilized to control the inflation rate of angioplasty balloons to achieve uniform expansion of a stenosis within a body lumen, and can also be used to uniformly deploy a stent within the same lumen.

It should be appreciated by those skilled in the art that while the embodiments described herein show a particular number and shape of fins utilized in the housing of the device, a variety of different shapes, sizes and number of fins can be utilized to achieve the desired features and flow rates without departing from the spirit and scope of the present invention. Additionally, the size and shape of the ball poppet can be varied to achieve desired flow rates within the regulator valve. Moreover, the shape of the control chamber and the housing also could be made in a number of shapes and sizes to provide the beneficial flow features and characteristics achieved by the present invention.

It will become apparent from the foregoing that, while particular forms of the invention have been illustrated and described, various modifications can be made without departing from the spirit and scope of the present invention. Accordingly, it is not intended that the invention be limited, except as by the appended claims.

What is claimed is:

1. A flow regulator for regulating flow of an inflation fluid to a balloon catheter, comprising:

a housing having a distal end for connection with the balloon catheter, a proximal end with a proximal flow orifice for connection with an inflation device and formed with a control chamber of a predetermined transverse cross-section and configured at the distal end with a distal flow orifice; and a restrictor in the control chamber operable in response to fluid flow in a first flow direction in the control chamber toward the distal flow orifice to cooperate with the distal flow orifice to form a first flow area for flow therethrough at a first flow rate and operative in response to fluid flow in the opposite direction in the chamber to move away from the distal flow orifice to cooperate in forming a second flow area larger than the first flow area for fluid flow in the direction opposite the first flow direction at a second flow rate greater than the first flow rate.

2. The flow regulator of claim 1, wherein:

the housing is formed with a distal orifice having a transverse cross-section less than the predetermined cross-section.

3. The flow regulator of claim 1, wherein:

the restrictor is in the form of a poppet; and the housing includes a stop located with the control chamber to be engaged by the poppet to limit travel within the control chamber.

4. The flow regulator of claim 3, wherein:

the poppet is round and is compressible to be, when engaged with the distal stop, compressed upon application of a selected high pressure by the inflation fluid in the chamber to reduce the flow area between the poppet and the distal orifice.

5. The flow regulator of claim 3, wherein:

the poppet is perforated so as to allow at least some amount of inflation fluid to flow therethrough.

6. The flow regulator of claim 3, wherein:

the housing includes an annular array of fins located at the distal end configured to define the distal stop.

7. The flow regulator of claim 3, wherein:

the housing includes an annular array of fins located at the proximal end is configured to retain the poppet in the chamber.

8. The flow regulator of claim 3, wherein:

the housing includes an annular array of fins located at both the proximal and the distal ends to retain the poppet in the control chamber.

9. The flow regulator of claim 5, wherein:

the fins are formed with radially inner guide edges that angle distally and radially inwardly to direct the poppet radially inwardly as it is moved in the first flow direction.

10. The flow regulator of claim 5, wherein:

the fins extend radially and are spaced annularly apart form each other.

11. The flow regulator of claim 1, wherein:

the balloon catheter is a stent delivery catheter.

12. A flow regulator for regulating flow of an inflation fluid to a balloon catheter, comprising:

a housing formed integral with a balloon delivery catheter, wherein the housing comprises:

a distal end in fluid communication with the expansion member;

a proximal end having a proximal orifice for connection with an inflation device;

a control chamber configured within the housing with a distal orifice; and a restrictor in the chamber operable in response to fluid flow in a first direction in the chamber toward the distal orifice to cooperate with the distal orifice to form a first flow area for flow therethrough at a first flow rate and operative in response to fluid flow in the opposite direction in the chamber to move away from the orifice to cooperate in forming a second flow area larger than the first flow area for flow in the direction opposite the first direction at a second flow rate greater than the first flow rate.

13. The flow regulator of claim 12, wherein:

the body is formed with the flow chamber having a cross-sectional flow area larger than that of the orifice; and the restrictor includes a poppet carried floatably in the chamber and shiftable from a flow restricting position relative to the orifice to a free flow position in the chamber.

14. A flow regulator for regulating flow of an inflation fluid to a balloon catheter, comprising:

a housing having a distal end with a distal flow orifice in fluid communication with the balloon catheter, a proximal end with a proximal flow orifice in fluid communication with inflation means, wherein the housing has a control chamber; and a restrictor in the control chamber which is operable in response to fluid flow in a first flow direction towards the distal flow orifice to cooperate with the distal flow orifice to form a first flow area for flow therethrough at a first flow rate and operative in response to fluid flow in a direction towards the proximal flow orifice to cooperate in forming a second flow area larger than the first flow area for fluid flow in a direction towards the proximal orifice at a second flow rate which is greater than the first flow rate.

15. The flow regulator of claim 14, wherein:

the restrictor is in the form of a poppet; and the housing includes a stop located within the control chamber to be engaged by the poppet to limit travel within in the control chamber.

16. The flow regulator of claim 14, wherein:

the inflation means is a hand held inflation device and the flow regulator is build into the inflation device.

17. The flow regulator of claim 14, wherein:

the flow regulator is built into a proximal hub which forms part of the balloon catheter.

18. A method of implanting an expandable intra-luminal stent including;

delivering the stent by an inflatable delivery balloon to a selected site in a lumen of a patient;

connecting the balloon to an inflation system including a flow control valve of the type limiting flow of a selected inflation fluid in one direction toward the balloon to a selected flow rate and operable to flow the fluid in the opposite direction at a greater flow rate;

flowing the fluid at the selected flow rate through the valve to the balloon to expand the stent at a selected rate; and flowing the fluid in an opposite direction at a greater flow rate to deflate the balloon.

19. The method of claim 18, further including;

while flowing the fluid in the one direction, reducing the flow rate in response to increased fluid pressure.

20. The method of claim 19, further including;

while flowing the fluid in one direction, shifting a poppet.

21. The method of claim 19, further including;

flowing the fluid through a perforated poppet.

* * * * *